(12) United States Patent
Lee

(10) Patent No.: US 7,035,684 B2
(45) Date of Patent: Apr. 25, 2006

(54) METHOD AND APPARATUS FOR MONITORING HEART FUNCTION IN A SUBCUTANEOUSLY IMPLANTED DEVICE

(75) Inventor: Brian B. Lee, Golden Valley, MN (US)

(73) Assignee: Medtronic, Inc., Minneapolis, MN (US)

( * ) Notice: Subject to any disclaimer, the term of this patent is extended or adjusted under 35 U.S.C. 154(b) by 486 days.

(21) Appl. No.: 10/376,062

(22) Filed: Feb. 26, 2003

(65) Prior Publication Data

US 2004/0167416 A1 Aug. 26, 2004

(51) Int. Cl.
*A61B 5/04* (2006.01)

(52) U.S. Cl. ...................................... 600/513

(58) Field of Classification Search ............ 607/18–20, 607/28, 36, 37; 600/513–515, 485, 486
See application file for complete search history.

(56) References Cited

U.S. PATENT DOCUMENTS

| | | | |
|---|---|---|---|
| 5,010,888 A | 4/1991 | Jadvar et al. | |
| 5,156,154 A | 10/1992 | Valenta et al. | |
| 5,188,106 A | 2/1993 | Nappholz et al. | |
| 5,313,953 A | 5/1994 | Yomtov et al. | |
| 5,518,001 A | 5/1996 | Snell | |
| 5,554,177 A | 9/1996 | Kieval et al. | |
| 5,570,671 A | 11/1996 | Hickey | |
| 5,702,427 A | 12/1997 | Ecker et al. | |
| 5,935,081 A | 8/1999 | Kadhiresan | |
| 5,987,352 A | 11/1999 | Klein et al. | |
| 6,351,670 B1 | 2/2002 | Kroll | |
| 6,366,811 B1 | 4/2002 | Carlson | |
| 6,409,674 B1 * | 6/2002 | Brockway et al. | 600/486 |
| 6,409,675 B1 | 6/2002 | Turcott | |
| 6,421,565 B1 | 7/2002 | Hemmingsson | |
| 6,650,940 B1 * | 11/2003 | Zhu et al. | 607/28 |

(Continued)

FOREIGN PATENT DOCUMENTS

WO  WO 90/04942 A1  5/1990

(Continued)

OTHER PUBLICATIONS

Magalski, A., et al., Continuous Ambulatory Right Heart Pressure Measurements with an Implantable Hemodynamic Monitor: A Multicenter, 12-month Follow-up Study of Patients with Chronic Heart Failure, *Journal of Cardiac Failure*, vol. 8, No. 2, 2002, pp. 63-70.

(Continued)

*Primary Examiner*—George Manuel
(74) *Attorney, Agent, or Firm*—Paul H. McDowall; Michael C. Soldner; Girma Wolde-Michael

(57) ABSTRACT

A minimally invasive, implantable monitor and associated method for chronically monitoring a patient's hemodynamic function based on signals sensed by one or more acoustical sensors. The monitor may be implanted subcutaneously or submuscularly in relation to the heart to allow acoustic signals generated by heart or blood motion to be received by a passive or active acoustical sensor. Circuitry for filtering and amplifying and digitizing acoustical data is included, and sampled data may be continuously or intermittently written to a looping memory buffer. ECG electrodes and associated circuitry may be included to simultaneously record ECG data. Upon a manual or automatic trigger event acoustical and ECG data may be stored in long-term memory for future uploading to an external device. The external device may present acoustical data visually and acoustically with associated ECG data to allow interpretation of both electrical and mechanical heart function.

38 Claims, 11 Drawing Sheets

U.S. PATENT DOCUMENTS

2002/0188329 A1   12/2002   Struble

FOREIGN PATENT DOCUMENTS

WO    WO 00/51492    8/2000

OTHER PUBLICATIONS

Xiao, S., et al., "Studying the Significance of Cardiac Contractility Variability", *IEEE Engineering in Medicine and Biology*, May/Jun. 2000, pp. 102-105.

Xiao, Y., et al., "The Phonocardiogram Exercise Test A Noninvasive and Inexpensive Method for Detecting Changes of Cardiac Reserve Based on Heart Sound Signal Processing", *IEEE Engineering in Medicine and Biology*, Jul./Aug. 1999, pp. 111-115.

Abdel-Alim, O., et al., "Heart Disease Diagnosis Using Heart Sounds", *Nineteenth National Radio Science Conference, Alexandria*, Mar. 19-21, 2002, pp. 634-640.

Myint, W., et al., "An Electronic Stethoscope with Diagnosis Capability", *IEEE*, 2001, pp. 133-137.

Xiao, S., et al., "Studying Cardiac Contractility Change Trend to Evaluate Cardiac Reserve", *IEEE Engineering in Medicine and Biology*, Jan./Feb. 2002, pp. 74-76.

Upshaw, C. et al., "Alfred Lewis Galabin and the First Human Documentation of Artrioventricular Block", *The American Journal of Cardiology*, vol. 88, Sep. 1, 2001, pp. 547-550.

Webster, J.G., *Medical Instrumentation: Application and Design*, 1992, pp. 378-407 and pp. 422-426.

Cobbold, R., *Transducers for Biomedical Measurements*, 1974, pp. 275-318.

Luisada, AA., et al., "Assessment of Left Ventricular Function by Noninvasive Methods", *Adv Cardiol*, vol. 32, 1985, pp. 111-141.

* cited by examiner

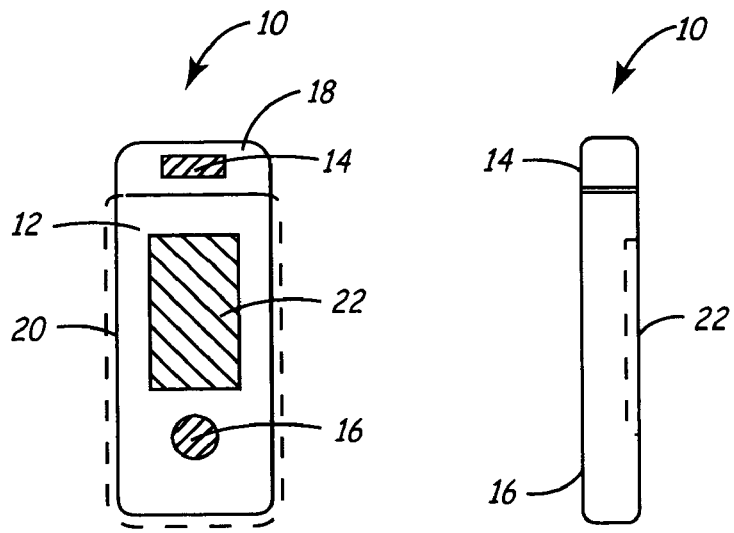
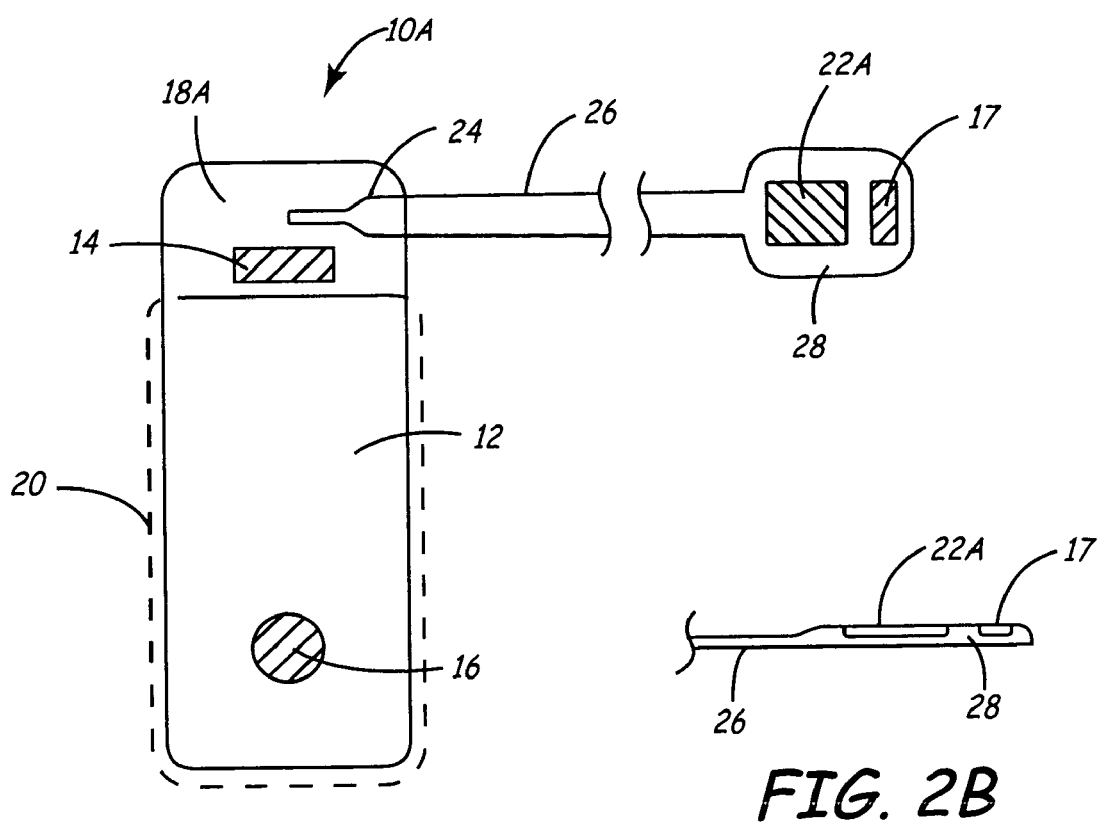

METHOD AND APPARATUS FOR MONITORING HEART FUNCTION IN A SUBCUTANEOUSLY IMPLANTED DEVICE

CROSS-REFERENCE TO RELATED APPLICATION

Cross-reference is hereby made to commonly assigned related U.S. Application, filed concurrently herewith, Ser. No. 10/376,063, entitled "APPARATUS AND METHOD FOR CHRONICALLY MONITORING HEART SOUNDS FOR DERIVING ESTIMATED BLOOD PRESSURE".

FIELD OF THE INVENTION

The present invention relates to implantable medical devices and, in particular, the present invention relates to an implantable medical device subcutaneously implanted for monitoring the hemodynamic function of a patient's heart using an acoustical sensor.

BACKGROUND OF THE INVENTION

Chronic monitoring of heart function can provide valuable diagnostic information for a variety of cardiovascular conditions, including arrhythmias, heart failure, syncope or other autonomic system abnormalities, etc. For example, chronic monitoring of the ECG subcutaneously, using a device such as the Reveal® Insertable Loop Recorder available from Medtronic, Inc., can be useful in diagnosing infrequent symptomatic episodes such as unexplained syncope and for capturing asymptomatic arrhythmias, which may be of interest to the patient's physician. Adding a monitor of hemodynamic function to ECG information would allow a physician to monitor and diagnose a larger spectrum of cardiac conditions that may or may not include arrhythmic events as seen in the subcutaneous ECG. In addition, a hemodynamic signal may allow the physician to continue to track the heart rate when the subcutaneous ECG becomes difficult to interpret due to electrical interference from artifacts such as loss of electrode contact, muscle noise or electromagnetic interference (EMI).

Numerous measurements may be made to gain an indication of hemodynamic function such as blood pressure, blood flow, wall motion, ventricular volume, or other measurements. These types of measurements are commonly made during a clinical examination and may involve both invasive and non-invasive procedures. For example, non-invasive ultrasound measurements may be made to investigate heart chamber volumes, heart wall motion, or blood flow velocities using Doppler ultrasound techniques. Principles and techniques for ultrasound instrumentation and measurements in cardiac applications are known and generally described in: *Medical Instrumentation: Application and Design*, ed. J. G. Webster (Houghton Mifflin Company, Boston) 1992, pp. 422–436 and *Transducers for Biomedical Measurements*, ed. R. Cobbold (John Wiley and Sons, New York) 1974, pp. 275–318. While clinical examinations are useful for patient assessment, they are limited in that they reflect the patient's condition only at a particular time on a particular day. Repeated examinations may be performed but the same measurement may not be repeated in exactly the same way because of slight differences in the sensor position and angle of the microphone or ultrasonic probe.

Chronic hemodynamic monitoring may be performed using implantable devices. For example blood pressure can be measured directly by placing a pressure sensor in the cardiovascular system, such as in the right ventricle. A chronically implantable device for monitoring the intracardiac electrogram (EGM) and right ventricular blood pressure has been implanted in chronic heart failure patients and used to continuously monitor their hemodynamic condition. See Magalski A, et al., J. Card. Fail., 2002;8(2):71–3. Apparatus for monitoring syncope including electrodes for recording electrical activity and/or blood pressure data of the patient's heart is generally disclosed in U.S. Pat. No. 6,351,670 issued to Kroll. An ambulatory cardiac diagnostic unit is generally disclosed in PCT Publication No. WO 90/04942, issued to Baker et al., which monitors heart action using intracardiac electrogram and pressure sensed using an intracardiac lead. These systems advantageously provide chronic heart monitoring but involve placement of a lead with pressure sensors in the patient's heart.

An implantable cardiac monitoring and therapy device which chronically monitors a patient's hemodynamic status as indicated by a cardiac contractility parameter which is derived from the result of performing Doppler ultrasound interrogation of cardiac tissue is generally disclosed in U.S. Pat. No. 5,156,154, issued to Valenta, Jr., et al. A Doppler ultrasound transducer affixed to a catheter is implanted within the right heart for assessing the motion of cardiac myofibril tissue within the heart, contributing to the pumping performance of the left ventricle. Other implantable devices for monitoring the hemodynamic status of a patient that include placing an ultrasound probe in the heart are described in U.S. Pat. No. 5,188,106 issued to Nappholz et al., and U.S. Pat. No. 6,421,565 issued to Hemmingson.

Placement of a pressure sensor, ultrasonic probe, accelerometer, microphone, or any other type of hemodynamic sensor, in the heart or anywhere within or along the cardiovascular system is a relatively invasive procedure. Indirect methods of measuring blood pressure, or other indices of hemodynamic function allow a sensor to be placed outside of the cardiovascular system with the measured signal being correlated to hemodynamic status. An implantable pulse generator having a pressure wave sensor mounted in the pulse generator in relation to the proximal end of a pacing lead for sensing pressure waves transmitted from the distal end of the pacing lead is generally described in U.S. Pat. No. 5,702,427, issued to Ecker et al. The pressure wave sensor is employed by a capture verification system to detect pressure waves associated with heart contraction. A pressure sensor is not positioned within the heart itself, however, this system still requires a lead to be placed in the heart to transmit pressure waves.

The use of extravascular sensors for use in determining hemodynamic status in an implantable device has also been proposed, which avoid the invasiveness of placing a hemodynamic sensor in the cardiovascular system. An implantable monitor for monitoring the hemodynamic status of a patient having extravascular sensors including vascular plethysmography, heart and lung sounds, thoracic impedence and ECG is generally disclosed in U.S. Pat. No. 6,409,675, issued to Turcott. A cardiac stimulating apparatus and method is generally described in U.S. Pat. No. 6,366,811, issued to Carlson, that non-intrusively determines an amount indicative of hemodynamic pulse pressure from an accelerometer signal. The accelerometer transmits a signal to the controller associated with fluid and myocardial accelerations of the patient's heart. The amount indicative of pulse pressure is used to optimize cardiac performance.

Acoustic waves, both within and outside of the human auditory range, can provide significant information relating to heart function. *Medical Instrumentation: Application and*

*Design* ed. J. G. Webster (Houghton Mifflin Company, Boston) 1992, pp. 378–407. Contraction of the whole heart can produce relatively low frequency sound waves, and blood flow and valve opening and closure produce relatively higher frequency sound waves. These sound waves are advantageously transmitted through the body such that they may be measured at a location relative to the heart but not necessarily in the heart. Recording acoustical data, such as heart sounds, ultrasonic echoes or otherwise, on a chronic basis could provide useful information relating to a patient's hemodynamic function. See Luisada et al., "Assessment of Left Ventricular Function by Nonivasive Methods", Adv-Cardiol vol. 32, 1985, pp. 111–141. An apparatus for adjusting the timing of pacing pulses delivered by an implanted cardiac pacer based on acoustic intensity of a particular heart sound received from an acoustic sensor, which may be placed against the sternum or in the pectoral region of the chest but outside the thoracic cavity, is described in U.S. Pat. No. 5,554,177, issued to Kieval et al., incorporated herein by reference in its entirety.

It is desirable, therefore, to provide a minimally invasive, implantable hemodynamic monitor that allows acoustical data related to the hemodynamic status of the patient to be recorded and stored. Such data may be used for diagnostic or therapy evaluation purposes and may be evaluated alone or in conjunction with ECG data to interpret both the electrical and mechanical function of the heart.

SUMMARY OF THE INVENTION

The present invention provides a minimally invasive, implantable hemodynamic monitor equipped with an acoustic sensor for detecting pressure waves that can be correlated to heart function. A range of low frequency sounds generated, for example, by heart wall motion, to high frequency sounds generated, for example, by blood flowing through valves or arteries, may be acquired. The analog signals generated by one or more acoustic sensors are digitized and processed such that a sampled digital signal may be stored in a temporary looping memory buffer. An automatic or manual trigger event may cause the data to be written to a long-term memory buffer and stored until uploaded to an external device. The stored data may be presented acoustically and/or visually by the external device. The data may be further analyzed by an external microprocessor to derive a number of measures of hemodynamic function.

An implantable hemodynamic monitoring device in accordance with the present invention is equipped with an acoustic sensor, ECG electrodes, a memory for storing acoustic and ECG data, and a microprocessor based controller for processing data and controlling device functions. An acoustic sensor may be provided as a passive sensor that does not require a power supply such as an accelerometer or piezoelectric sensor. An additional or alternative acoustic sensor may be provided as an active sensor requiring a power supply, such as a miniaturized microphone or an ultrasound transmitter and receiver. The acoustic sensor may be mounted within the device housing or header block, on the external surface of the housing or header block, or on a subcutaneous lead extending from the device.

An implant location for the device is carefully selected to achieve optimal acoustic signal quality. The acoustic sensor is preferably located such that the sensor reception range has a limited directionality and is focused toward the heart, and more preferably focused on the major acoustic signal generating components of the heart or great vessels, such as the valves, ventricular wall, ascending aorta or otherwise.

The acoustic sensor signal is received by an input circuit including appropriate amplifiers and filters for isolating the acoustical signals of interest and reducing or eliminating sounds associated with other organs, respiration, muscle or skeletal motion, voice, etc. Both low frequency components, in the range of 0.04 Hz to 50 Hz, and higher frequency components, in the auditory range of approximately 50 Hz to 5 KHz may be of interest, although most of the energy in the heart signal is at frequencies less than 250 Hz.

In one embodiment, acoustical data is received over a wide range of frequencies from a passive sensor with broad-band filtering so as to retain both high and low frequency information that may be related to hemodynamic function. Sampled data are stored when triggered by a manual patient trigger or by an automatic trigger such as an arrhythmia detection or other automatically detected event. The acoustical data may then be uploaded to an external device for signal processing in which custom variable bandpass filtering can be used to select which components of the acoustical data the user is interested in viewing. Acoustical data may be stored concurrently with ECG data such that cyclic acoustical events may be directly associated with the electrical heart rhythm.

For an alternative heart and blood flow monitoring signal, an active ultrasound sensor (with a frequency between 1 and 10 MHZ) may be provided as a single transmitter/receiver incorporated in the implanted device or carried by a lead extending from the device. The single transmitter/receiver may be operated in a burst send/receive mode such that a burst of sound waves of a desired frequency are transmitted to a targeted heart location and the reflected echoes are received by the same transmitter/receiver. Alternatively, a separate receiver may be incorporated in the device or carried by a lead extending from the device such that the transmitter may continuously send an ultrasonic signal that is continuously received by the receiver. Ultrasonic sensor positioning and anchoring are important in optimizing the received energy and in repeatability of measurements made. Interference from dense bones, such as the ribs or sternum, is preferably avoided. Transmission and reception through the suprasternal notch or any of the intercostal spaces in close proximity to the heart may be effective.

In order to reduce the power requirements of the device to make it practical for a chronic, subcutaneous implant, the ultrasound system may be duty cycled such that snippets of the Doppler signal are collected at desired intervals rather than continuously. The ultrasonic sensor may alternatively be activated only when triggered by a manual or automatic event trigger, such as an arrhythmia detected from the ECG signal.

Thus a device and method are provided that allow minimally invasive, chronic hemodynamic monitoring of the heart for diagnostic or therapy evaluation purposes. The device may advantageously be placed subcutaneously or submuscularly without requiring sensors to be placed within the cardiovascular system.

BRIEF DESCRIPTION OF THE DRAWINGS

FIG. 1A is an illustration of a subcutaneously implantable device 10 for storing ECG and acoustical data received from a passive acoustical sensor according to one embodiment of the present invention.

FIG. 1B is a side view of the device of FIG. 1A.

FIG. 2A is an illustration of an alternative embodiment of a subcutaneously implantable device for storing ECG and acoustical data according to the present invention.

FIG. 2B is a side view of a sensor assembly included in the embodiment of FIG. 2A.

DETAILED DESCRIPTION OF THE INVENTION

Figure 3:
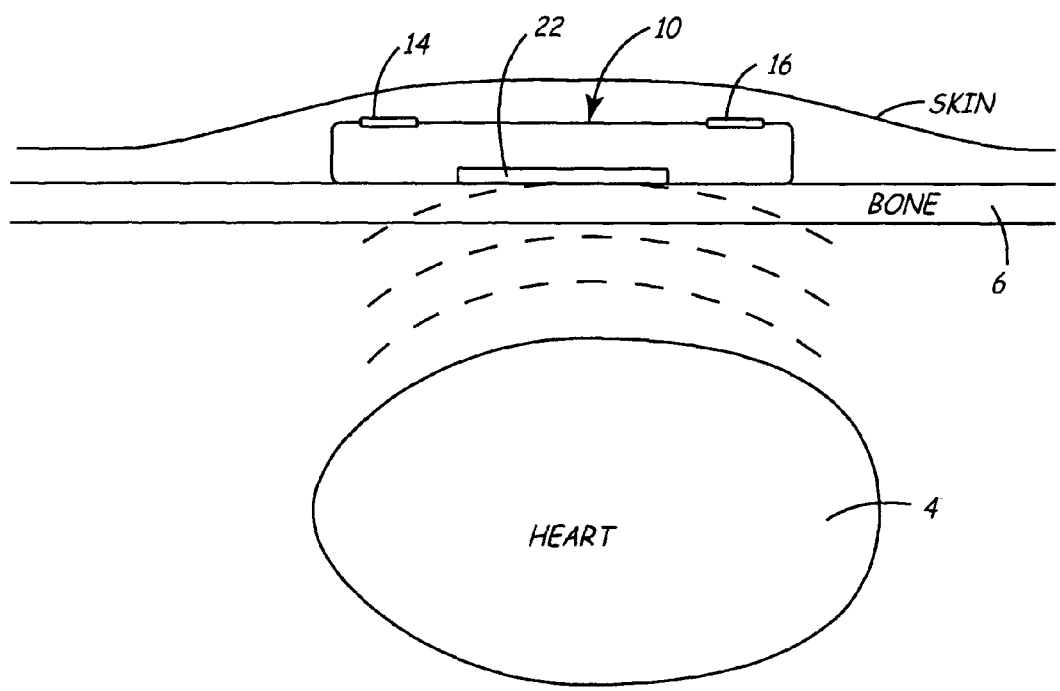
FIG. 3 is an illustration of the device of FIG. 1 implanted subcutaneously in relation to a patient's heart for receiving acoustical signals.

FIGS. 1A and 1B illustrate a front and side view of a minimally invasive implantable device 10 for chronically monitoring heart function. The size and shape of device 10 may be generally provided as disclosed in U.S. Pat. No. 5,987,352, issued to Klein et al., incorporated herein by reference in its entirety. The device 10 is provided with a hermetically sealed housing or "can" 12 preferably formed from a biocompatible metal such as titanium and closed at one end by a plastic cap member 18. Cap member 18 may be formed of materials similar to those used for pacemaker connector blocks, such as polyurethane or epoxy. Housing 12 is provided with an insulative coating 20, indicated by dashed line, formed from an insulating material, such as a Parylene coating. Device 10 preferably includes at least two electrodes 14 and 16 for sensing a patient's subcutaneous ECG. Electrode 14 is formed from a biocompatible conductive metal such as platinum, iridium, titanium, or alloys thereof. Electrode 14 may be mounted in cap member 18 with an exposed surface for detecting the patient's ECG and is electrically connected to a conductive feed-through to an internal circuit board, described below in reference to FIG. 4. Electrode 16 may be formed as an uninsulated portion of the housing 12 by creating an opening in the insulative coating 20. Electrode 16 is also electrically coupled to an internal circuit board.

Device 10 is further provided with an acoustic sensor 22 in accordance with the present invention. In one embodiment, acoustic sensor 22 is a passive sensor that does not require an energizing power supply, such as an accelerometer, or a piezoelectric material, which may be a piezoelectric crystal, ceramic or film. In another embodiment, acoustic sensor 22 may be provided as an active sensor that requires a power supply such as a miniaturized, implantable microphone or an ultrasound transmitter/receiver. Device 10 may be provided with two or more acoustic sensors, which may be any combination of passive or active acoustical sensors. An advantage of providing a passive sensor is that the battery size required by device 10 may be minimized, reducing the overall size of device 10 making it easier to implant under the skin and more comfortable for the patient. However, signals received by a passive sensor may be not be isolated to a specific heart region. An advantage of an ultrasonic sensor is that an isolated area of the heart may be monitored but at the expense of increased power consumption and signal processing.

Sensor 22 may be mounted on the internal surface of the device housing 12, as shown in the side view of FIG. 1B. Sensor 22 is electrically coupled to an internal circuit board, described below in reference to FIG. 4. In alternative embodiments, sensor 22 may be located in the header 18 or attached to the external surface of housing 12.

FIG. 2A is an illustration of an alternative embodiment of a minimally invasive heart function monitor. Identically numbered components in FIG. 2A correspond to those shown in FIG. 1, however, in this embodiment acoustical sensor 22A is mounted on a low-profile sensor assembly 28 carried at the distal end of a lead 26. Lead 26 is connected at its proximal end to the header 18A. Header 18A is provided with a connector bore for receiving lead 26. Sensor assembly 28 may optionally carry an additional ECG electrode 17. Electrode 17 may be used in combination with electrodes 14 and 16 for sensing different vectors of the ECG. Multi-electrode ECG sensing in an implantable monitor is described in U.S. Pat. No. 5,313,953 issued to Yomtov, et al., incorporated herein by reference in its entirety.

FIG. 2B is a side view of the sensor assembly 28 showing assembly 28 having a relatively flat profile such that assembly 28 is easily implanted under the skin. Because device 10 may be relatively thicker than sensor assembly 28, device 10 may not be as comfortably positioned at various subcutaneous implant sites, such as over the ribs or sternum, as sensor assembly 28. Thus, sensor assembly 28 allows acoustic sensor 22A to be implanted at a site for receiving optimal acoustic signals that may not be a practical site for device 10 implantation due to patient discomfort, such as the ribs or sternum.

FIG. 3 is an illustration of the device 10 implanted subcutaneously in relation to a patient's heart for receiving acoustical signals. In this arrangement, acoustic sensor 22 is placed against bony tissue 6 directed toward the patient's heart 4. In preliminary experiments, the inventor has found that placement of a passive acoustical sensor, such as an accelerometer, against bone such as the rib or the sternum can improve phonocardiographic components of the acoustical signal compared to when the accelerometer is placed against soft tissue. The bone can enhance coupling of components of the sound waves from the heart into the acoustic sensor. The signal amplitude received when an accelerometer was placed against the sternum or ribs was greater than when the sensor was placed against soft tissue. Other types of acoustical sensors, such as an ultrasonic sensor, may be better positioned over a soft tissue site to avoid reflection of the transmitted ultrasonic waves as will be described in greater detail below.

Figure 4:
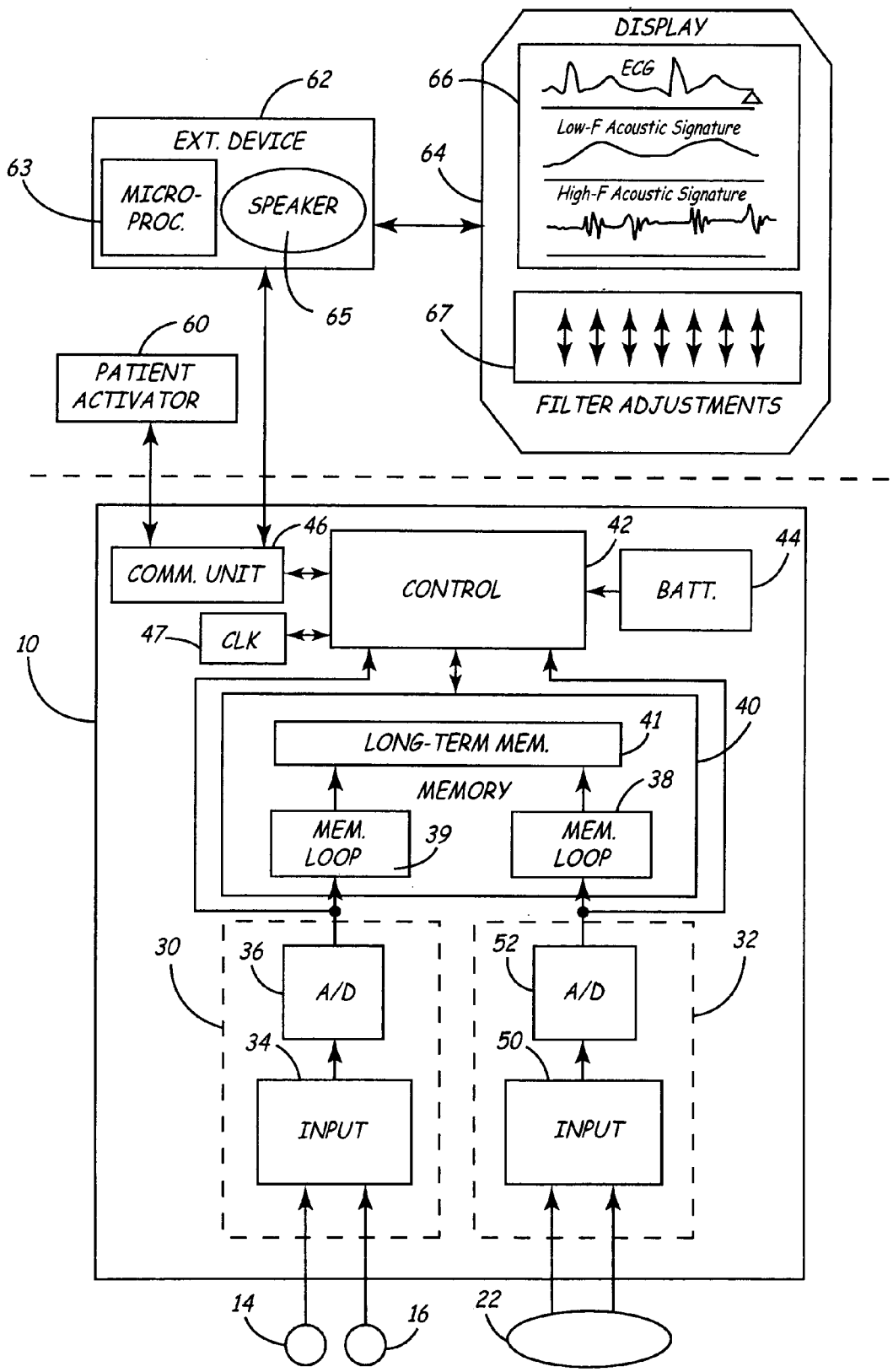
FIG. 4 is a high-level block diagram of circuitry included in device 10 of FIG. 1 and an external device in communication with the implanted device.

FIG. 4 is a high-level block diagram of circuitry included in device 10 of FIGS. 1 and 2. Device 10 preferably includes an ECG monitoring channel 30 and an acoustic monitoring channel 32. ECG electrodes 14 and 16 bring a signal from the body to an input circuit 34, which includes amplifiers and filters for reducing noise and passing the ECG signals of interest. The output of input circuit 34 is fed to an A/D converter 36, which samples and digitizes the ECG signal, preferably at a sampling rate on the order of 100 Hz. Input circuit 34 and A/D converter 36 are included in ECG monitoring channel 30 of device 10. These components may be implemented in device 10 as described in the above-cited '352 patent issued to Klein, or as provided by other subcutaneous ECG monitoring systems known in the art.

Acoustic monitoring channel 32 includes an input circuit 50 for receiving signals from acoustic sensor 22. Input circuit 50 includes filters and amplifiers for improving the signal-to-noise ratio of cardiac-related acoustical signals by filtering noise due to respiration, muscle or skeletal motion, voice, etc., and passing and amplifying the acoustical signals of interest associated with heart wall motion, valve motion or blood flow. A/D converter 52 samples and digitizes the signal received from input circuit 50. A preferred sampling rate is at least twice the highest frequency of interest, in accordance with the well-known Nyquist criterion.

Output from A/D converters 36 and 50 are received by memory 40. Memory 40 preferably includes temporary memory buffers 38 and 39 which continuously record ECG and acoustical data in a looping fashion. Temporary memory buffers preferably have at least a 128 Kbyte capacity. Because acoustical data may be sampled at a higher rate than ECG data, looping memory 38, designated for storing acoustical data, may be provided with a greater capacity than looping memory buffer 39, designated for storing ECG data.

Output from A/D converters 36 and 50 may also be received by control unit 42. Control unit 42 may be provided as a microprocessor based control system for controlling the operations of device 10. Control unit 42, and any other circuits or acoustical sensors included in device 10 that require a power supply, are powered by battery 44. Control unit 42 is in communication with memory 40 for controlling the storage of ECG and acoustical data in long-term memory 41. A real time clock or counter 47 provides control unit 42 with time information that can be used for marking stored data such that events may be temporally identified. Long-term storage of data may be triggered by automatic or manual triggers. As such, control unit 42 receives signals from communications unit 46 which may receive a signal from an external patient activator 60 for manually triggering long-term storage of ECG and acoustical data.

Patient activator 60 may take the form of a handheld device that is battery-powered and uses coded radio-frequency telemetric signals transmitted upon depressing a button, to trigger data storage by the device 10. A patient, or another person nearby, may use the handheld device when the patient feels symptomatic or has become unconscious. A handheld device may alternatively be provided having a magnet that closes a magnetic switch within device 10 when held in the vicinity of device 10 to elicit a data storage trigger signal. Alternative embodiments for a patient activated trigger can include light activation, sonic activation or mechanical activation by finger tapping or slapping. Various modes of patient activated triggering are described in the above-cited '352 patent.

If a patient trigger is used it is advantageous to provide feedback to the patient regarding whether the attempt to trigger long term storage of the event was successful. To accomplish this the implant should telemeter out a signal that indicates it has recognized a valid trigger. (This of course requires additional circuitry and usage of the limited available power supply.) The external triggering device then notifies the patient via the triggering device or through some known alarm mechanism whether they have or have not properly triggered the implanted device. This notification can be one of any combination of a number of feedback methods including: one or two visual sources such LED's, an auditory source such as a beeping speaker in one or two tones, or a tactile source such as a vibration. See also U.S. Pat. No. 5,518,001, incorporated herein by reference in its entirety, for other potential trigger-indicator ideas for a hand-held patient activated trigger device.

Control unit 42 may also generate automatic trigger signals for triggering the long-term storage of data. For example, control unit 42 may be equipped with algorithms for identifying ECG events, such as R-waves, T-waves, and/or P-waves from data received from A/D converter 36. Based on these events, control unit 42 may detect the occurrence of arrhythmias, including asystole, bradycardia, tachycardia, and fibrillation. Arrhythmia detection algorithms known in the field of implantable cardioverter defibrillator technologies may be incorporated in control unit 42. A detected arrhythmia may elicit an automatic trigger to initiate the storage of ECG and acoustical data.

Alternatively, or additionally, control unit 42 may be equipped with algorithms for detecting a change in an acoustical signal, which may be associated with heart wall motion, valve motion, blood flow or otherwise, and generate an automatic trigger for the long-term storage of data based on that change. In a basic embodiment, a flat line acoustical signal may be used to trigger long-term data storage. In more elaborate schemes, control unit 42 may process acoustic data received from A/D converter 52 to correlate aspects of the received signal to an index of heart function. A change in heart function, as indicated by the acoustical signal, beyond a certain threshold or predetermined range of normal values may be used to trigger long-term data storage.

Alternatives to the overall design shown in FIG. 4 may be considered. For example, certain functions performed by control unit 42 may be performed by integrated circuits. Integrated circuits for detecting a QRS signal from the sensed ECG and for detecting arrhythmias are described in the above-cited Klein patent.

Communication unit 46 is also able to communicate with an external device 62, which may generally take the form of a programmer, for delivering operational commands to device 10, receiving confirmation signals from device 10 that operational commands were received, and for receiving data uploaded from memory 40. Communications unit 46 should contain an antenna or other transceiver device or circuitry to communicate with an external device such as device 62. A clock or counter circuit 47 reports the time since start or real time to the external device 62 contemporaneously with a data uploading session so that the events recorded in memory 40 may be temporally pinpointed.

External device 62 may include a microprocessor 63 for processing digitized data received from device 10. In particular, acoustical data may be processed to separate frequencies associated with particular cardiac sounds, such as lower frequency sounds associated with heart wall motion from higher frequency sounds associated with valve motion and/or blood flow. Acoustical data may be displayed on a display unit 64, which may include an LCD screen 66 or other appropriate display, and a display controller 68. Display controller 68 is provided to allow the user to selectively adjust filters to vary the displayed acoustical data components. As illustrated on display screen 66, ECG data may be displayed graphically with corresponding low frequency and higher frequency acoustical data such that cyclic cardiac events generating acoustical signals, such as valve opening and closing, start of ventricular ejection or filling, and electrical events, may be identified as related to electrical heart function and mechanical heart function. Visual analysis of simultaneous baseline shifts in ECG data and acoustic data may allow the physician to identify major body events such as a fall, which may aid the physician in analyzing significant cardiac events.

In one embodiment, external device 62 may further include a speaker 65 for broadcasting uploaded acoustical data in the auditory range. Such data would include heart sound data that physicians are generally well trained in detecting and interpreting for diagnosing a variety of heart conditions. Acoustical data may thus be presented both visually on display unit 64 and acoustically through speaker 65 in a simultaneous fashion to enhance the physician's ability to interpret the data. Custom variable bandpass filtering of acoustical data using filter adjustments 67 allows a physician to select the frequency components that are displayed and/or broadcast, thus allowing analysis and interpretation of select components of the acoustical data.

According to the present invention, sensor 22 may be positioned as described in *Medical Instrumentation: Application and Design* ed. J. G. Webster (Houghton Mifflin Company, Boston) 1992, pp. 378–407, incorporated herein by reference in its entirety.

Figure 5A:
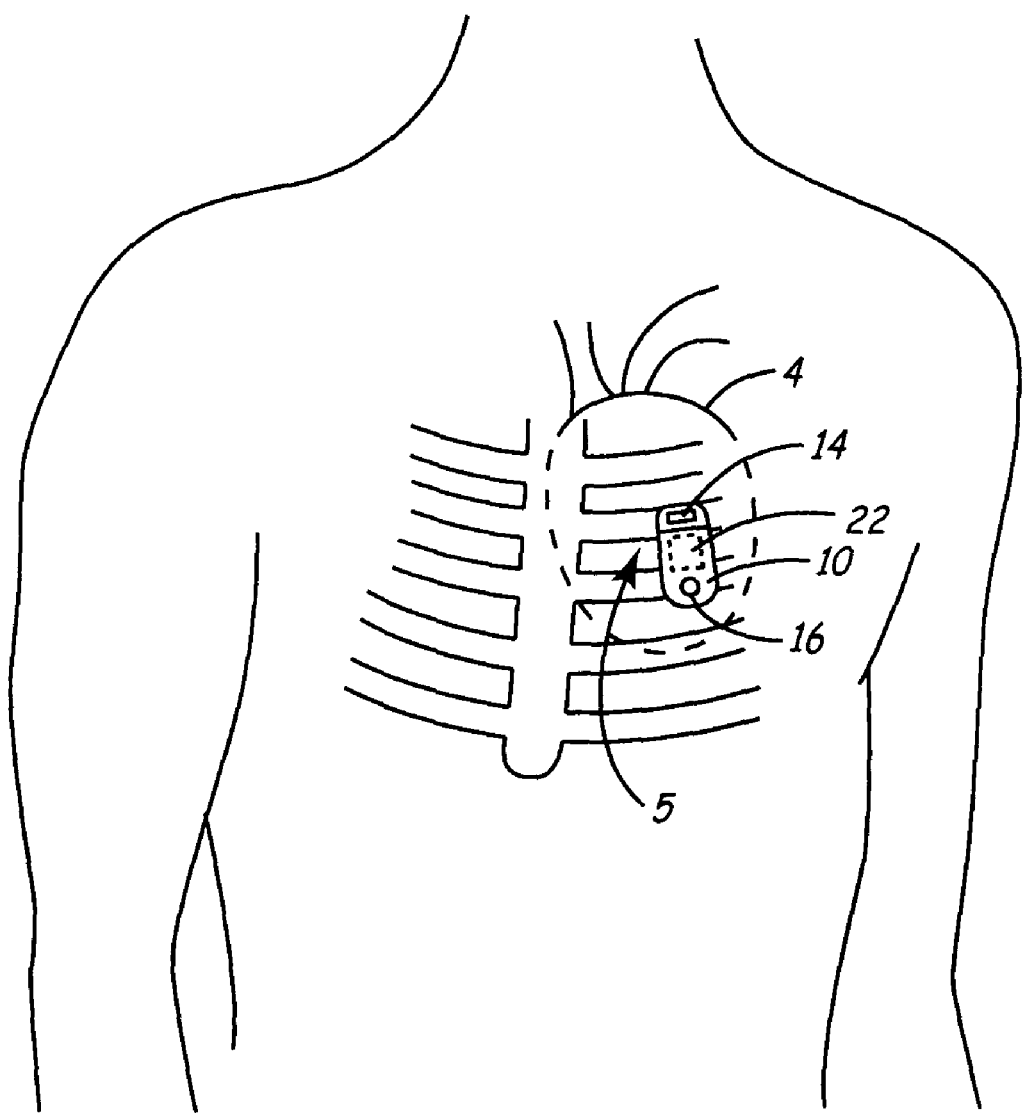
FIGS. 5A and 5B illustrate possible arrangements for including an ultrasonic sensor in a subcutaneously implantable device for monitoring heart function.
Figure 5B:
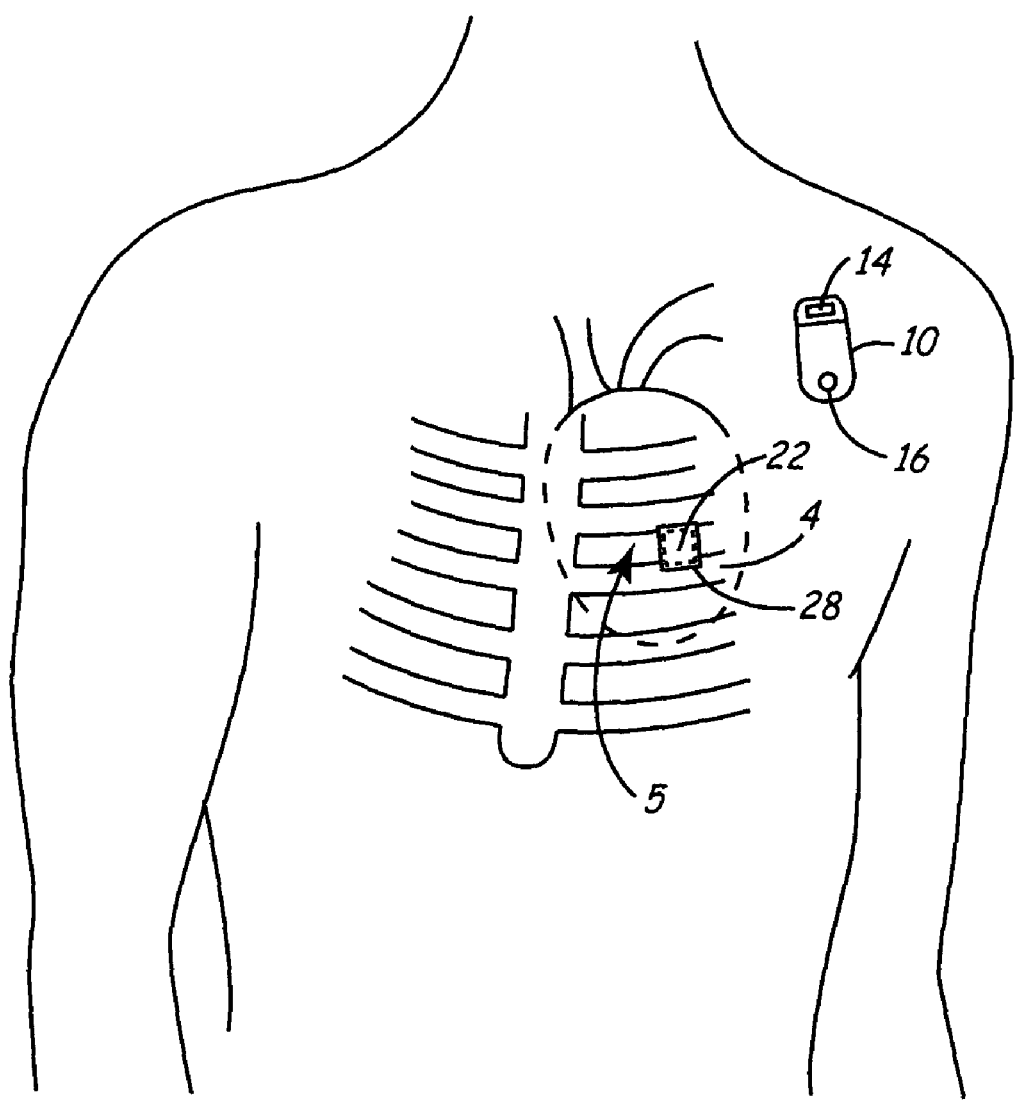

FIGS. 5A and 5B illustrate possible arrangements for including an ultrasonic sensor in a subcutaneously implantable device for monitoring heart function. In FIG. 5A, acoustic sensor 22 is provided as a piezoelectric transmitter and receiver of ultrasonic energy with a frequency between 1 and 10 MHz. Sensor 22 operates in an alternating burst send and receive mode under the control of control unit 42. Ultrasonic sound waves are transmitted in a burst by sensor 22 and the echoes produced by the ultrasound waves reflecting off heart or blood constituents are then received. Sensor 22 is preferably located over soft tissue such that bone does not reflect the transmitted ultrasonic energy, preventing it from reaching the heart or great vessels. Device 10 is shown, therefore, in a location over the ribs such that sensor 22 is aligned with an intercostal space 5. An alternative arrangement is shown in FIG. 5b in which sensor 22 is located on low-profile sensor assembly 28 coupled to lead 26 extending from device 10. Sensor assembly 28 may be anchored in a position over the ribs with sensor 22 positioned over an intercostal space 5. The intercostal space at which sensor 22 is positioned may be selected based on the region of the heart from which wall motion of blood flow measurements are desired. In the configuration of FIG. 5B, the device 10 may advantageously be positioned away from the rib cage, in the pectoral region, which, depending on the size of device 10, may be more comfortable for the patient.

As is well known in the ultrasound field, heart motion and/or blood flow primarily parallel to the ultrasound beam and within the beam will reflect echoes from the blood constituents or heart tissue as movement occurs toward or away from the ultrasound transducer. Echoes are extracted over a short range and at a desired depth through proper time-gating of the received signal and classic pulsed Doppler processing. The final result of this Doppler processing is a low frequency audible signal proportional to the velocity of movement of the primary reflectors within the beam and over the gated range, referred to herein as "gated Doppler volume."

In order to maintain a reliable Doppler signal during chronic monitoring, it is important to maintain the implanted device in a fixed position through proper anchoring methods such as suturing, so that the gated Doppler volume encompasses the section of heart and blood flow desired to be viewed. A trade-off is made between enlarging this zone to make it robust to changes in heart position with posture and eliminating undesired Doppler signals from other moving structures. Selection of transducer size, transmitting frequency, and range from the implant to the target volume, all influence the cross-sectional area of the gated Doppler volume. The depth of the ultrasound beam is controlled by the frequency of the transmitted energy. Lower frequencies will penetrate more deeply than higher frequencies. Thus, transmitting a set of frequencies over a predetermined range will allow blood or heart motion at selected distances from the sensor 22 to be detected. Motion in an isolated area of the heart may therefore be chronically monitored.

Figure 5C:
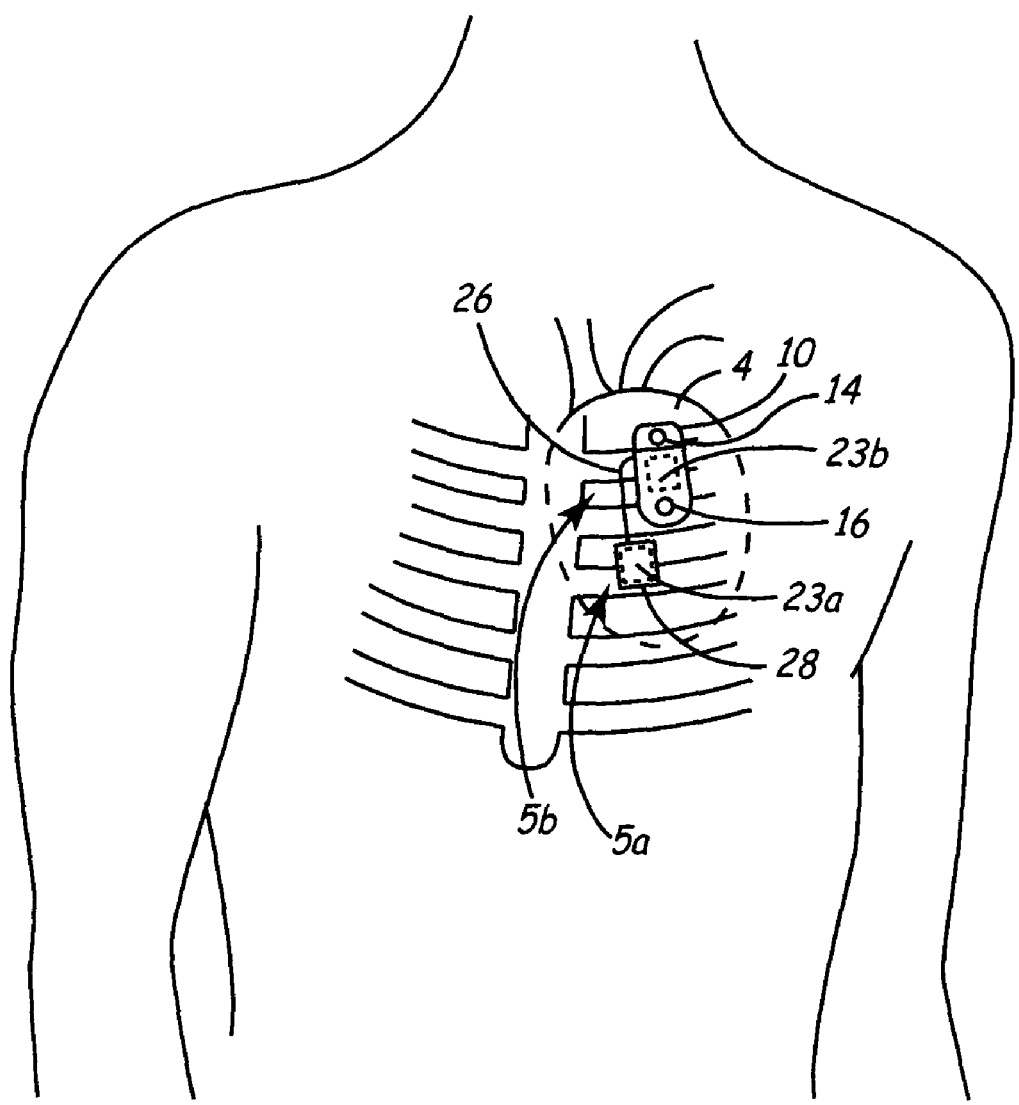
FIG. 5C is an illustration of an ultrasonic sensor including a transmitter and a separate receiver.

FIG. 5C is an illustration of an ultrasonic sensor including a transmitter and a separate receiver. An ultrasonic transmitter 23a is located on a low-profile sensor assembly 28 extending from device 10 on a lead 26. A separate receiver 23b is located on device 10. The transmitter 23a may alternatively be located on device 10 and the receiver 23b on the low-profile assembly 28. In still other embodiments, transmitter 23a and receiver 23b may both be located on low-profile sensor assembly 28 or both located on device 10. In yet another alternative embodiment, transmitter 23a may be located on a sensor assembly on one lead extending from the device 10 and a separate receiver 23b may be located on a sensor assembly on a second lead extending from the device 10.

In the embodiment shown in FIG. 5c, the transmitter 23a may be located over an intercostal space 5a to transmit ultrasonic energy toward the heart, and the receiver 23b may be positioned over the same or a different intercostal space 5b to receive reflected echoes through the intercostal space. When provided separately, transmitter 23a and receiver 23b may operate in a continuous mode such that heart or blood motion may be continuously monitored.

Figure 5D:
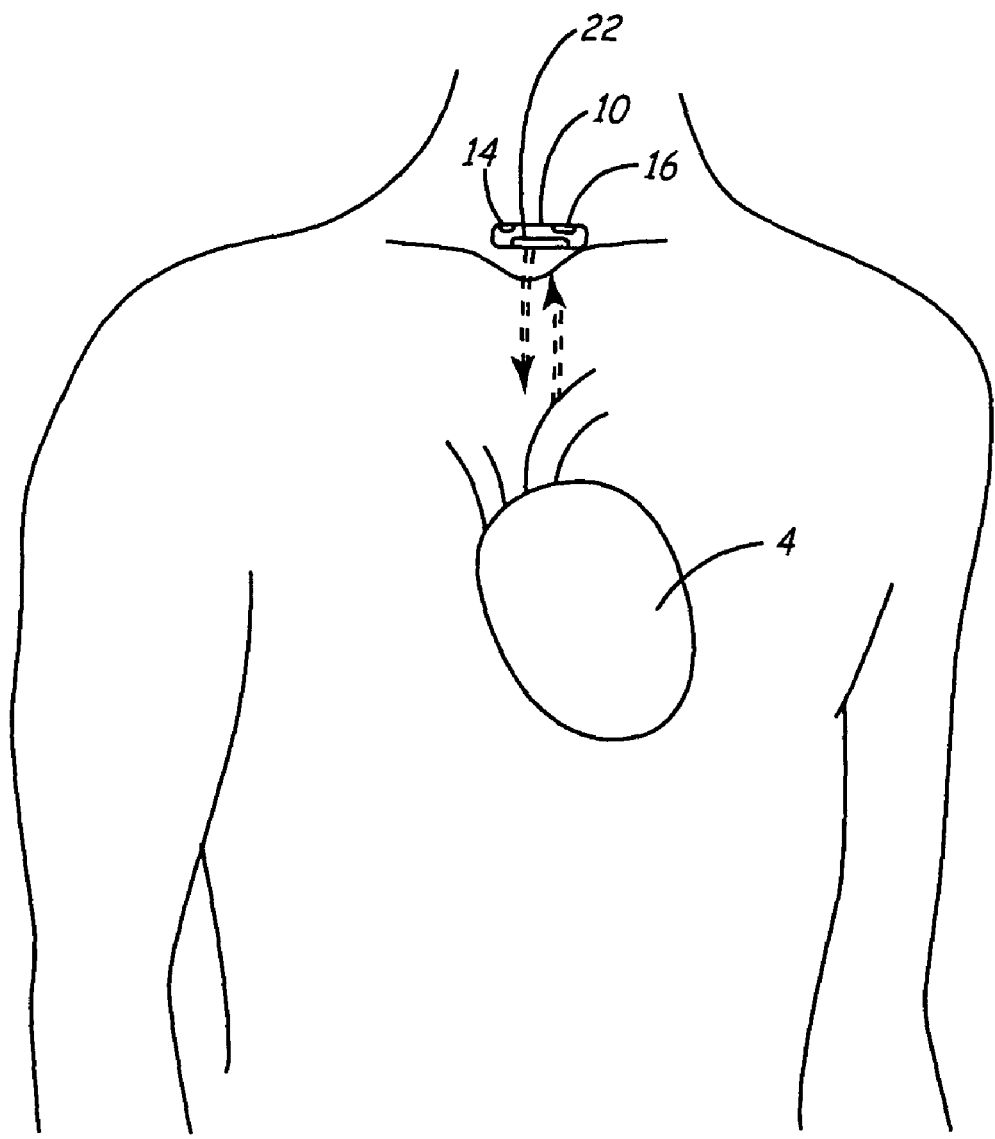
FIG. 5D, 5E and 5F are illustrations of alternative implant positions of a heart function monitor provided by the present invention.
Figure 5E:
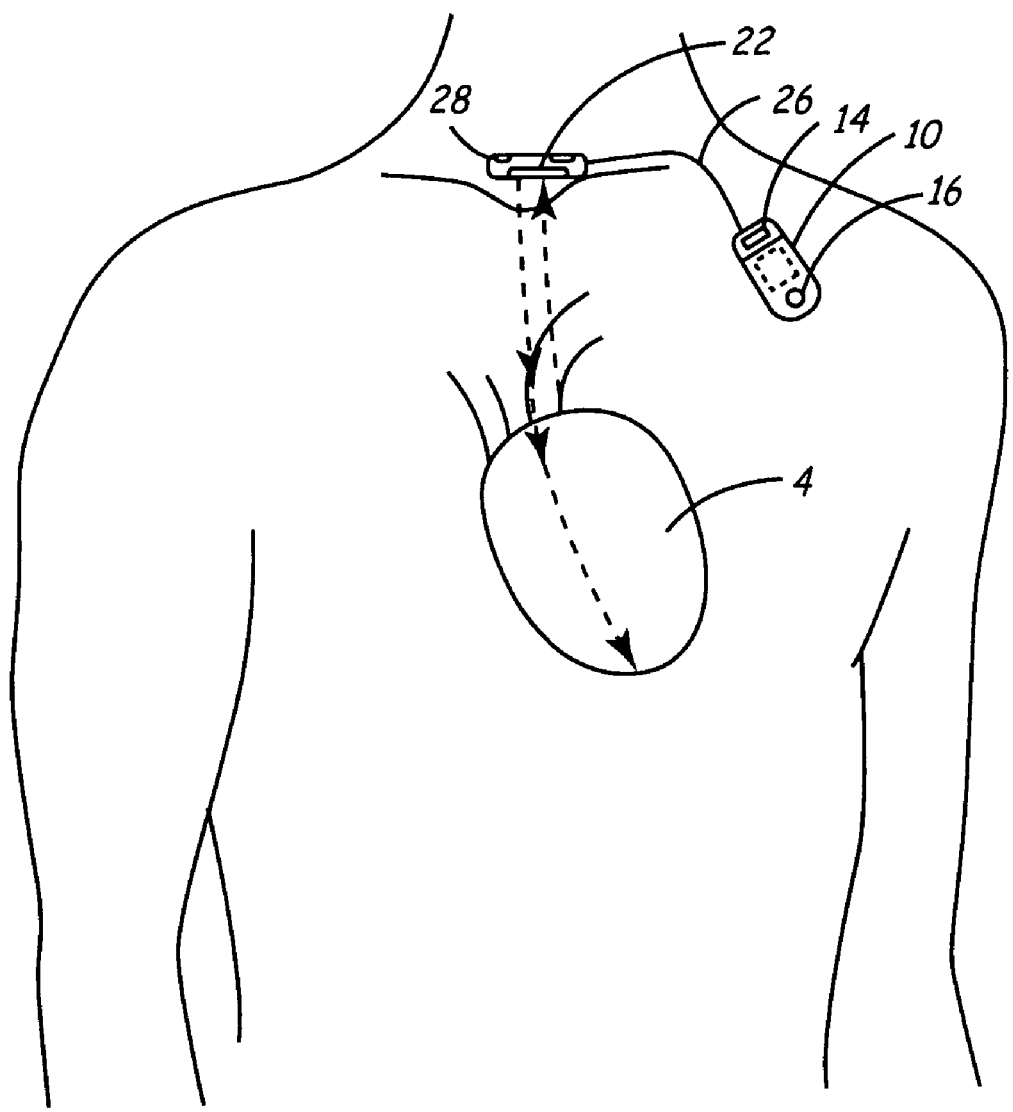
Figure 5F:
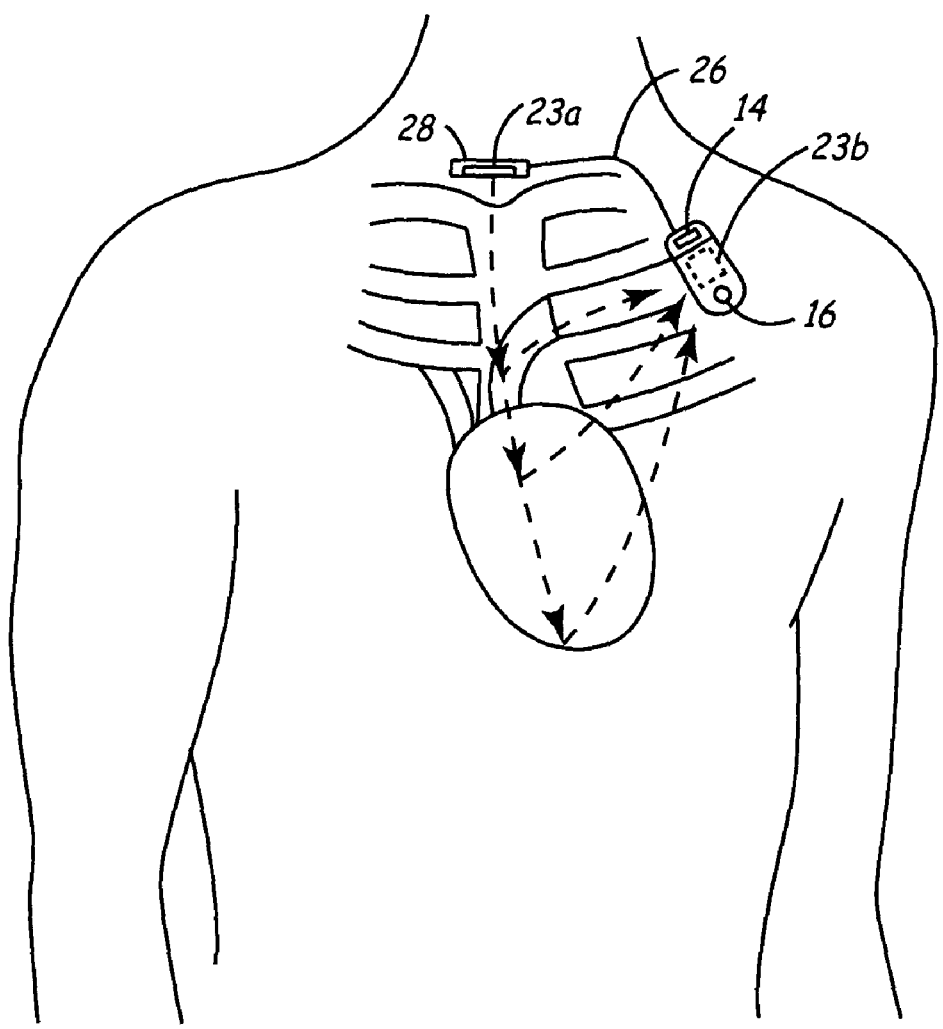

Alternative locations for positioning an ultrasonic sensor for receiving good acoustical signals from the heart or great vessels include positioning a sensor over the suprasternal notch. In FIG. 5D, device 10 is shown in a location over the suprasternal notch and positioned such that ultrasonic waves may be transmitted from sensor 22 downward toward the heart and aortic outflow tract. An alternative arrangement is shown in FIG. 5E in which the sensor 22 may be located on a low-profile lead 26 extending from the device 10. Sensor 22 may be positioned over the suprasternal notch and device 10 may be positioned in the pectoral region or any area that is comfortable for the patient that allows connection to the lead 26. In FIG. 5F, a transmitter 23b is located over the suprasternal notch to transmit ultrasonic energy down toward the heart as indicated by dashed arrows, and receiver 23b, located on device 10, is positioned to receive reflected echoes through an intercostal space. While the configurations illustrated in FIGS. 5D through 5F may provide good acoustical signals related to heart wall motion or blood flow, the area over the suprasternal notch is generally sensitive, and chronic implantation of a device at this site may not be well-tolerated by the patient. The configurations of FIGS. 5A through 5C described above, in which an ultrasonic sensor is aligned with an intercostal space, are believed to be more practical for chronic implantation with minimal patient discomfort.

In order to meet practical power requirements for an implantable system, an ultrasonic sensor preferably operates according to an on/off duty cycle. The on/off duty cycle may include an on time of 1 minute and an off time of 59 minutes so that monitoring occurs 24 times a day with average power of 60× less than the peak measurement power.

To further reduce power requirements, the ultrasonic sensor may be powered to monitor heart function only upon an automatic or manual triggering event. For example, when an arrhythmia is detected by device 10 resulting in a long-term data storage trigger, the ultrasonic sensor may be powered to receive acoustical signals that may be stored simultaneously with ECG data.

Device 10 makes chronic hemodynamic monitoring possible by storing acoustical data received from the heart during episodes or events that may be of interest to the physician. The device may continuously or intermittently record acoustical data in a looping memory. A manual or automatic trigger causes the device to save a predetermined interval of acoustical data in long-term memory. Corresponding ECG data is preferably stored simultaneously. A manual trigger may be delivered by the patient subsequent to feeling symptomatic (e.g. dizziness, short of breath, palpitations, etc.).

In one embodiment, operational modes for data storage triggering are programmable to allow patient triggering only and/or one or more types of automatic triggers for data storage. An interval of data, preferably on the order of 5 or more minutes for manual triggers and 1 or more minutes for automatic triggers, is stored. The data interval may include data stored in the temporary memory buffers prior to the trigger event and data following the trigger event. It should be considered that with automatic triggering, the determination by the device of an event worth recording and the subsequent activation of the trigger by the device itself will be faster than the patient finding his device for activation or otherwise activating the device, so the pre-trigger time record can be smaller.

Figure 6:
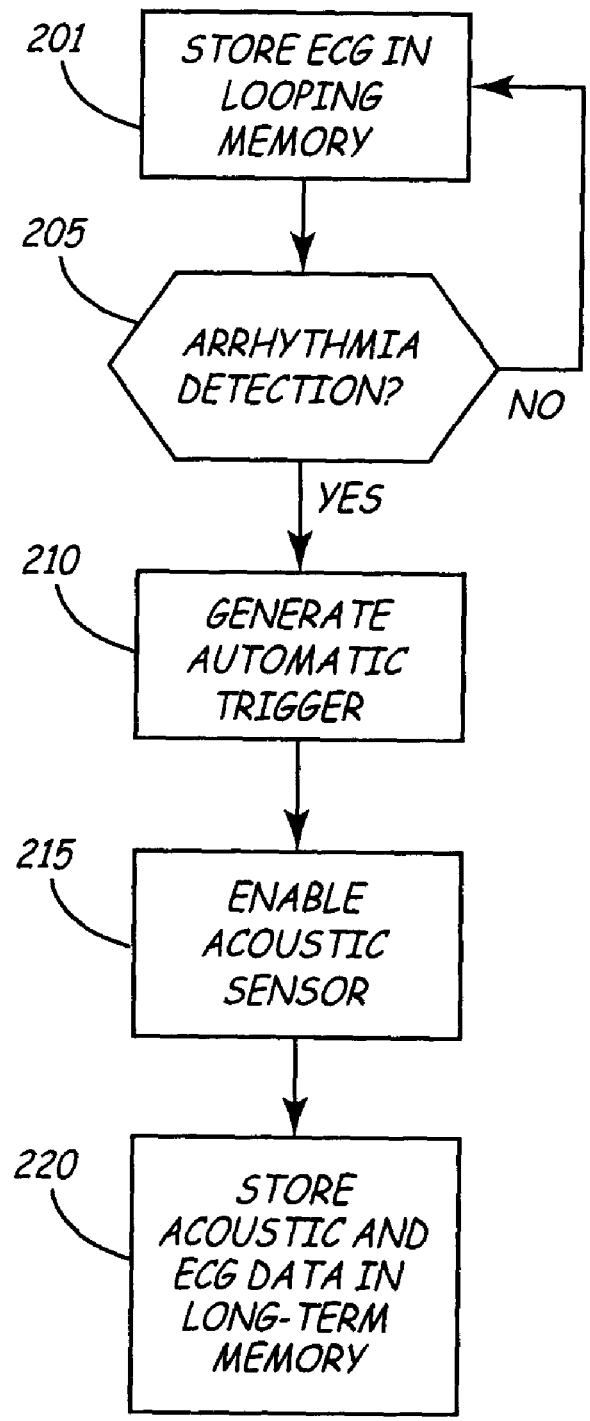
FIG. 6 is a flowchart summarizing the operations performed by the device of FIG. 1 during an automatic trigger mode of operation in one embodiment of the invention.

FIG. 6 is a flowchart summarizing the operations performed by device 10 during an automatic trigger mode of operation in one embodiment of the invention. Beginning at step 201, the ECG signal sensed by electrodes 14 and 16 is sampled by A/D converter 36 and stored in temporary looping memory buffer 39.

The sampled ECG signal is simultaneously analyzed by control unit 42 to determine if an arrhythmia, which may be asystole, bradycardia, tachycardia, fibrillation, premature contractions etc., is present. If an arrhythmia is detected at decision step 205, an automatic trigger signal is generated by control unit 42 at step 210. The trigger signal first enables acoustic sensor 22. In this embodiment, acoustic sensor 22 may be an active sensor, such as a miniaturized microphone or ultrasonic sensor that is preferably enabled only following a triggering event in order to conserve device battery power. The trigger signal next causes data stored in temporary memory buffer 39 to be written to long-term memory 41 at step 220 and continues to write sampled acoustic and ECG data received from A/D converters 36 and 52 to a designated area of long-term memory 41 for a predetermined interval of time following the trigger signal.

Depending on the long-term memory capacity, a limited number of triggered events may be stored between uploading data sessions. Preferably at least three events of five minutes may be stored. Additional triggered events may overwrite the oldest stored event if uploading has not occurred and long-term memory is full. The number of events that may be stored may be increased by storing data in a compressed format. Data compression may be at a compression ratio of 2:1 or some other device supported ratio. When setting the operational mode of the device, the physician or attendant can decide whether to record data in a compressed mode or not. If greater detail of the ECG or acoustical data is required than can be developed from compressed data storage, the physician should select non-compressed recording, thereby limiting the time available to record. In some embodiments the sampling rate may be modified as well, for both ECG sampling and acoustical data sampling. Many types are known compression algorithms could be used. An excellent example is found in the article Arrhythmia Detection Program for an Ambulatory ECG Monitor by Mueller, copyright 1978, ISA, ISBN 876645, incorporated herein by reference in its entirety.

In an alternative embodiment, both ECG and acoustic data may be written to temporary, looping memory buffers 39 and 38 simultaneously until a manual or automatic trigger occurs. An automatic trigger may optionally be based on a change in the detected acoustical data indicating a change in hemodynamic function or another change or event, such as a fall, which may be detected from the acoustical signal. Acoustic data can be a rich source of information including not only information relating to heart and blood motion, but also information relating to other body changes such as a fall, the presence of seizures, or resuscitation efforts. Such events may be recognizable by a shift in the acoustic signal baseline. Recognition and detection of these events may be of interest to a physician in interpreting a particular symptomatic event or sequence of events.

Figure 7:
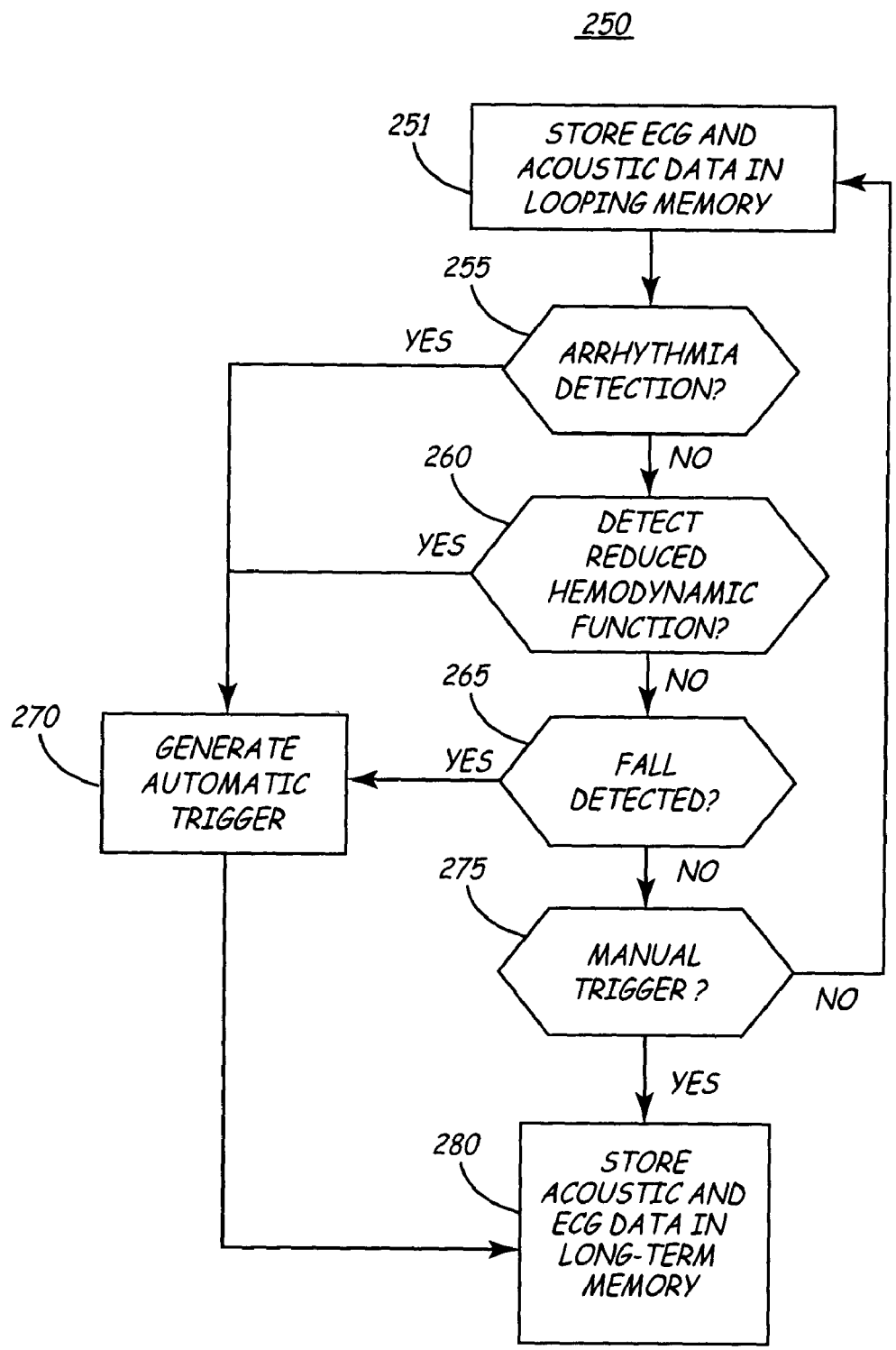
FIG. 7 is a flow chart summarizing operations performed by the device of FIG. 1 during an automatic triggering mode in another embodiment of the present invention in which acoustical data is used for automatic triggering.

FIG. 7 is a flow chart summarizing operations performed by device 10 during an automatic triggering mode in another embodiment of the present invention in which acoustical data is used for automatic triggering. At step 251, ECG and acoustical data are continuously written to temporary, looping memory buffers 39 and 38, respectively. ECG and acoustical data are received by control unit 42 from A/D converters 36 and 52, respectively. Control unit 42 analyzes the data in order to detect arrhythmias or compromised hemodynamic function or other changes that may be indicative of a whole body event such as a fall or seizure. If an arrhythmia is detected at decision step 255, an automatic trigger is generated at step 270. An interval of pre- and post-trigger ECG and acoustical data is stored in long-term memory at step 280.

If reduced hemodynamic function is detected at decision step 260, with or without a concurrent arrhythmia detection at decision step 255, an automatic trigger may be generated at step 270 based on the hemodynamic change. The hemodynamic change may be detected as a threshold crossing of a parameter derived from processed acoustical data. Under the control of control unit 42, acoustic and ECG data are written to long-term memory 41 at step 280 such that the data is available for future uploading to external device 62 for review by a physician.

Other events, such as a fall, a seizure, or resuscitative efforts, may also be detected for the purpose of automatic data storage triggering. For example, at step 265, a fall may be detected by a sudden baseline shift of the acoustical signal due to body impact. Detection of a fall may additionally cause an automatic trigger to be generated at step 270 with subsequent long-term data storage at step 280.

Monitoring for triggering events at steps 255, 260, and 265 are intended to be performed continuously and simultaneously such that if any ECG-related, hemodynamic-related, or fall-related automatic triggering event occurs at any time, ECG and acoustical data are stored in long-term memory at step 280. Furthermore, if a manual trigger is received by device 10 at any time during the monitoring for automatic triggers, as indicated at decision step 275, acoustic and ECG data are stored in long-term memory.

According to the method 250, long-term data storage is performed in response to manual triggers and multiple types of automatic triggers making device 10 more sensitive to detecting and storing events that may be of interest to a physician. ECG and hemodynamic data collected whenever a suspected arrhythmia, hemodynamic event, syncopal event, or symptomatic event occurs could provide valuable diagnostic information for a number of pathologic conditions.

Thus, a subcutaneously implantable heart function monitor has been described that allows hemodynamic function of the heart to be continuously or periodically monitored based on acoustical signals associated with heart motion or blood flow. Acoustical data, along with concurrent ECG data, may be stored in a looping memory until an automatic or manual triggering event occurs, causing the data to be stored in long-term memory until it is uploaded to an external device. The external device may perform additional signal processing to correlate the acoustical data to a hemodynamic measure of heart function. The external device may present the acoustical data, along with concurrent ECG data, both visually and acoustically. The device of the present invention, therefore, provides a physician with valuable diagnostic or therapy evaluation data that allows both the electrical activity of the heart and the hemodynamic function of the heart to be monitored chronically. Acoustic data may further provide a physician with information useful in understanding symptomatic events relating to heart movement, sudden body position changes, the presence of seizures, and evidence of resuscitation efforts. Specific embodiments of a minimally invasive heart function monitor based on acoustical and ECG sensing described herein are intended to be exemplary and should not be considered limiting with regard to the following claims.

The invention claimed is:

1. An implantable medical device for monitoring heart function of a patient's heart, comprising:
   a housing portion enclosing operative circuitry of the device;
   a plurality of electrodes, electrically coupled to the circuitry, configured for detecting cardiac depolarization events from one of a subcutaneous position extravascular and a submuscular position extravascular;
   a sensor, electrically coupled to the circuitry, configured for detecting pressure waves corresponding to the heart function from one of a subcutaneous and a submuscular position extravascular;
   a storage device storing data corresponding to the cardiac depolarizations and the pressure waves coupled to the operative circuitry; and
   a control unit controlling the sensor and storage of the data in the storage device in response to one of the detected cardiac depolarizations and the detected pressure waves.

2. The implantable medical device of claim 1, further comprising a communication unit configured for receiving a patient input, wherein the control unit controls the sensor and storage of the data in the storage device in response to the detected cardiac depolarizations, the detected pressure waves, and the patient input.

3. The implantable medical device of claim 1, further comprising;
   a sensor assembly including the sensor; and
   a coupling device electrically coupling the sensor assembly to the housing portion, the sensor assembly having a first thickness and the housing portion having a second thickness greater than the first thickness.

4. The implantable medical device of claim 3, wherein the sensor includes a transmitter and a receiver, one of the transmitter and the receiver positioned along the sensor assembly and the other of the transmitter and receiver positioned along the housing portion.

5. The implantable medical device of 3, wherein the sensor includes a transmitter and a receiver, both the transmitter and the receiver positioned along one of the sensor assembly and the housing portion.

6. The implantable medical device of claim 1, wherein the sensor is adapted to be positioned along soft tissue between the housing and the heart.

7. The implantable medical device of claim 1, wherein the sensor is adapted to be positioned along a suprasternal notch.

8. The implantable medical device of claim 1, wherein the sensor is adapted to be positioned over an intercostal space.

9. The implantable medical device of claim 3, wherein the sensor assembly is adapted to be positioned along a suprasternal notch.

10. The implantable medical device of claim 3, wherein the sensor assembly is adapted to be positioned over an intercostal space.

11. The implantable medical device of claim 3, wherein the plurality of electrodes includes a first electrode and a second electrode positioned along the housing portion, and a third electrode positioned along the sensor assembly.

12. The implantable medical device of claim 1, wherein the storage device includes a first memory portion and a second memory portion, and wherein the control unit stores simultaneously detected cardiac depolarizations and corresponding pressure waves in the first memory portion.

13. The implantable medical device of claim 12, wherein the storage unit stores the data stored in the first memory portion and subsequently detected cardiac depolarizations and detected pressure waves in the second memory portion in response to one of the detected cardiac depolarizations and the detected pressure waves.

14. The implantable medical device of claim 13, wherein the detected pressure waves are indicative of one of hemodynamic events of the heart and physical activity of the patient.

15. The implantable medical device of claim 13, wherein the control unit stores data stored in the first memory portion and subsequent detected cardiac depolarizations and detected pressure waves in the second memory portion in response to a patient activation.

16. A method of monitoring heart function of a patient's heart from one of a subcutaneous and a submuscular position extravascular, comprising the steps of:
   detecting cardiac depolarizations from one of a subcutaneous and a submuscular position extravascular and storing data corresponding to the detected cardiac depolarizations in a first memory portion;
   determining whether a cardiac event is detected in response to the detected depolarizations; and
   detecting pressure waves corresponding to the heart function from one of a subcutaneous and a submuscular position extravascular, storing the data stored in the first memory portion and subsequently detected cardiac depolarizations and detected pressure waves in a second memory portion in response to a cardiac event being detected.

17. The method of claim 16, wherein the step of detecting cardiac depolarizations further comprises detecting the pressure waves simultaneously with the cardiac depolarizations and storing data corresponding to the simultaneously detected pressure waves and cardiac depolarizations in the first memory portion.

18. The method of claim 17, further comprising the step of storing the data stored in the first memory portion and subsequently detected cardiac depolarizations and detected pressure waves in the second memory portion in response to one of the detected cardiac depolarizations and the detected pressure waves.

19. The method of claim 18, wherein the detected pressure waves are indicative of one of hemodynamic events of the heart and physical activity of the patient.

20. The method of claim 18, wherein data stored in the first memory portion and subsequently detected cardiac depolarizations and detected pressure waves are stored in the second memory portion in response to a patient activation.

21. An implantable medical device system device for monitoring heart function of a patient's heart from one of a subcutaneous and a submuscular position, extravascular comprising:
   a housing portion housing circuitry of the device;
   a plurality of electrodes, electrically coupled to the circuitry, adapted for detecting cardiac depolarizations from one of a subcutaneous and a submuscular position extravascular;
   a sensor, electrically coupled to the circuitry, adapted for detecting pressure waves corresponding to the heart function from one of a subcutaneous and a submuscular position; extravascular
   a storage device storing data corresponding to the cardiac depolarizations and the pressure waves;
   a control unit controlling the sensor and storage of the data in the storage device in response to the detected cardiac depolarizations and the detected pressure waves;
   an external device receiving and processing the stored data from the storage device; and
   a display unit couple to the external device displaying the cardiac depolarizations and the pressure waves.

22. The implantable medical device system of claim 21, wherein the pressure waves include low frequency and high frequency acoustic data, and wherein the detected cardiac depolarizations are displayed graphically on the display unit with the low frequency and high frequency acoustic data.

23. The implantable medical device system of claim 21, further comprising an acoustical output device coupled to the external device, and wherein the detected cardiac depolarizations are displayed graphically on the display unit and the corresponding pressure waves are output acoustically by the output device simultaneously with the displayed cardiac depolarizations.

24. The implantable medical device of claim 21, further comprising;
   a sensor assembly including the sensor; and
   a coupling device electrically coupling the sensor assembly to the housing portion, the sensor assembly having a first thickness and the housing portion having a second thickness greater than the first thickness.

25. The implantable medical device of claim 24, wherein the sensor includes a transmitter and a receiver, one of the transmitter and the receiver positioned along the sensor assembly and the other of the transmitter and receiver positioned along the housing portion.

26. The implantable medical device of 24, wherein the sensor includes a transmitter and a receiver, both the transmitter and the receiver positioned along one of the sensor assembly and the housing portion.

27. The implantable medical device of claim 24, wherein the sensor assembly is adapted to be positioned along a suprasternal notch.

28. The implantable medical device of claim 24, wherein the sensor assembly is adapted to be positioned over an intercostal space.

29. The implantable medical device of claim 24, wherein the plurality of electrodes include, a first electrode and a second electrode positioned along the housing portion, and a third electrode positioned along the sensor assembly.

30. The implantable medical device of claim 21, wherein the sensor is adapted to be positioned along soft tissue between the housing and the heart.

31. The implantable medical device of claim 21, wherein the sensor is adapted to be positioned along a suprasternal notch.

32. The implantable medical device of claim 21, wherein the sensor is adapted to be positioned over an intercostal space.

33. The implantable medical device of claim 21, wherein the storage device includes a first memory portion and a second memory portion, and wherein the control unit stores simultaneously detected cardiac depolarizations and corresponding pressure waves in the first memory portion.

34. The implantable medical device of claim 33, wherein the storage unit stores the data stored in the first memory portion and subsequently detected cardiac depolarizations and detected pressure waves in the second memory portion in response to one of the detected cardiac depolarizations and the detected pressure waves.

35. The implantable medical device of claim 34, wherein the detected pressure waves are indicative of one of hemodynamic events of the heart and physical activity of the patient.

36. The implantable medical device of claim 34, further comprising a patient activator, wherein the control unit stores data stored in the first memory portion and subsequently detected cardiac depolarizations and detected pressure waves in the second memory portion in response to a patient activation via the activator.

37. The implantable medical device system of claim 21, wherein the storage device includes a first memory portion and a second memory portion, wherein the control unit stores date corresponding to the detected cardiac depolarizations in the first memory portion, and stores the data in the first memory portion and subsequently detected cardiac depolarizations and corresponding detected pressure waves in the second memory portion in response to a cardiac event being detected.

38. An implantable medical device for monitoring heart function of a patient's heart from one of a subcutaneous and a submuscular extravascular position, comprising the steps of:
   means for detecting cardiac depolarizations from one of a subcutaneous and a submuscular extravascular position and storing data corresponding to the detected cardiac depolarizations in a first memory portion;
   means for determining whether a cardiac event is detected in response to the detected depolarizations; and
   means for detecting pressure waves corresponding to the heart function from one of a subcutaneous and a submuscular extravascular position storing the data stored in the first memory portion and subsequently detected cardiac depolarizations and detected pressure waves in a second memory portion in response to a cardiac event being detected.

* * * * *

UNITED STATES PATENT AND TRADEMARK OFFICE
CERTIFICATE OF CORRECTION

PATENT NO. : 7,035,684 B2  Page 1 of 1
APPLICATION NO. : 10/376062
DATED : April 25, 2006
INVENTOR(S) : Lee et al.

It is certified that error appears in the above-identified patent and that said Letters Patent is hereby corrected as shown below:

Claim 1, Col. 13, lines 37, 38 and 42, please delete "...position extravascular..." and insert --...extravascular position...--

Claim 16, Col. 14, lines 44, 46 and 53, please delete "...position extravascular..." and insert --...extravascular position...--

Claim 21, Col. 15, lines 13, 18 and 23, please delete "...position extravascular..." and insert --...extravascular position...--

Claim 29, Col. 16, line 2, please delete "...include, a..." and insert --...includes a...--

Claim 37, Col. 16, line 41, please delete "...stores date..." and insert --...stores data...--

Signed and Sealed this

Third Day of April, 2007

JON W. DUDAS
*Director of the United States Patent and Trademark Office*